(12) United States Patent
Gould

(10) Patent No.: US 12,036,393 B2
(45) Date of Patent: Jul. 16, 2024

(54) INJECTION DEVICES

(71) Applicant: Owen Mumford Limited, Oxford (GB)

(72) Inventor: Oliver Gould, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 23 days.

(21) Appl. No.: 16/097,511

(22) PCT Filed: Apr. 20, 2017

(86) PCT No.: PCT/GB2017/051097
§ 371 (c)(1),
(2) Date: Oct. 29, 2018

(87) PCT Pub. No.: WO2017/187140
PCT Pub. Date: Nov. 2, 2017

(65) Prior Publication Data
US 2019/0143041 A1    May 16, 2019

(30) Foreign Application Priority Data
Apr. 29, 2016    (GB) ...................................... 1607491

(51) Int. Cl.
*A61M 5/20*    (2006.01)
*A61M 5/32*    (2006.01)

(52) U.S. Cl.
CPC ............ *A61M 5/20* (2013.01); *A61M 5/2033* (2013.01); *A61M 5/3202* (2013.01);
(Continued)

(58) Field of Classification Search
CPC .......... A61M 2005/206; A61M 5/2033; A61M 2005/2013; A61M 2005/208; A61M 5/3202; A61M 5/3257
See application file for complete search history.

(56) References Cited

U.S. PATENT DOCUMENTS 9,604,003 B2 *    3/2017    Brereton ............. A61M 5/3158
2002/0173752 A1 *    11/2002    Polzin ................. A61M 5/1782
604/233

(Continued)

FOREIGN PATENT DOCUMENTS

EP    1125593 A1    8/2001
EP    2438941 A1 *    4/2012    .......... A61M 5/2033
(Continued)

OTHER PUBLICATIONS

International Search Report and Written Opinion, International Application No. PCT/GB2017/051097, mailed Jul. 17, 2017, 15 pages.

(Continued)

*Primary Examiner* — Scott J Medway
(74) *Attorney, Agent, or Firm* — Quarles & Brady LLP

(57) ABSTRACT

An injection device for delivering a dose of medicament from a syringe comprises a housing with a forward body and rearward body, the forward and rearward bodies being axially moveably interconnected. A drive mechanism is arranged, in use, to deliver a dose from the syringe, the drive mechanism being activated by a trigger. The injection device further comprises an interlock having a locked position in which activation of the drive mechanism by the trigger is prevented and an unlocked position in which the drive mechanism may be activated. The interlock arrangement is moved to the unlocked position by relative axial movement of the forward and rearward body caused by the injection device being urged against an injection site. The injection device further comprises an interlock hold arrangement associated with a forward facing skin abutment surface of the injection device. The interlock hold arrangement is configured to help maintain the alignment of the rearward and forward body when the interlock is in the unlocked (Continued)

position and the forward facing skin abutment surface is in contact with an injection site.

15 Claims, 8 Drawing Sheets

(52) U.S. Cl.
CPC ... *A61M 5/3213* (2013.01); *A61M 2005/2013* (2013.01); *A61M 2005/206* (2013.01); *A61M 2005/2073* (2013.01); *A61M 2005/208* (2013.01)

(56) References Cited

U.S. PATENT DOCUMENTS

| | | | | |
|---|---|---|---|---|
| 2005/0277885 | A1* | 12/2005 | Scherer | A61M 5/2033 604/136 |
| 2007/0135767 | A1* | 6/2007 | Gillespie | A61M 5/2033 604/135 |
| 2009/0312705 | A1* | 12/2009 | Grunhut | A61M 5/326 604/110 |
| 2010/0268170 | A1* | 10/2010 | Carrel | A61M 5/2033 604/198 |
| 2012/0053528 | A1* | 3/2012 | Bollenbach | A61M 5/24 604/192 |
| 2012/0203186 | A1* | 8/2012 | Vogt | A61M 5/326 604/192 |
| 2013/0172822 | A1* | 7/2013 | Ekman | A61M 5/2033 604/198 |
| 2013/0190722 | A1 | 7/2013 | Kemp et al. | |
| 2013/0281935 | A1* | 10/2013 | Kemp | A61M 5/3202 604/197 |
| 2013/0289525 | A1 | 10/2013 | Kemp et al. | |
| 2013/0296795 | A1* | 11/2013 | Ekman | A61M 5/326 604/197 |
| 2013/0317446 | A1* | 11/2013 | Hourmand | A61M 5/2033 604/196 |
| 2013/0345643 | A1* | 12/2013 | Hourmand | A61M 5/3232 604/198 |
| 2014/0135705 | A1* | 5/2014 | Hourmand | A61M 5/2033 604/196 |
| 2014/0257194 | A1* | 9/2014 | Edhouse | A61M 5/20 604/198 |
| 2015/0283323 | A1* | 10/2015 | Young | A61M 5/3287 604/182 |
| 2018/0250471 | A1* | 9/2018 | Grimoldby | A61M 5/31553 |
| 2018/0289899 | A1* | 10/2018 | Gould | A61M 5/326 |
| 2018/0333544 | A1* | 11/2018 | Ploch | A61M 5/345 |

FOREIGN PATENT DOCUMENTS

| | | | | |
|---|---|---|---|---|
| WO | WO-2009155277 | A1 * | 12/2009 | A61M 5/2033 |
| WO | WO-2012085580 | A1 * | 6/2012 | A61M 5/20 |
| WO | 2016051168 | A2 | 4/2016 | |

OTHER PUBLICATIONS

UK Intellectual Property Office Search Report, (from the priority application) Application No. GB1607491.6 filed Apr. 29, 2016, mailed Oct. 11, 2016, 3 pages.

* cited by examiner

INJECTION DEVICES

CROSS REFERENCE AND RELATED APPLICATIONS

This application represents the United States National Stage of International Application No. PCT/GB2017/051097, filed Apr. 20, 2017, which claims priority to United Kingdom Patent Application No. 1607491.6, filed Apr. 29, 2016, which is hereby incorporated by reference in its entirety.

FIELD OF THE INVENTION

This invention relates to injection devices for delivering a dose of medicament from a syringe. In particular, the invention relates an injection device including an "interlock" safety arrangement.

BACKGROUND OF THE INVENTION

Injection devices are used for the convenient administration of medicaments. For example, injection devices (which may typically be in the form of a pen injector) may be used for providing a single metered dose of a medicament, such as Epinephrine, in an emergency or for providing regular metered doses of a medicament, such as Insulin. Such devices may be either single use "disposable" devices in which the device is typically provided with a syringe already installed, and which is not user-replaceable, or "reusable" devices which allow the user to replace the syringe when the medicament has been used.

It may be noted that whilst the term "syringe" is used herein for clarity and consistency, the skilled person will appreciate that this term is intended to be broadly interpreted. In some arrangements the syringe may for example be a cartridge (which, for example, may be arranged to receive a disposable needle) or other medicament container. In some arrangements the syringe/cartridge/medicament container may formed integrally with the (or part of the) injection device.

Injection devices may be provided in the form of an "autoinjector" device in which, in addition to automating the delivery of the medicament, the device is also arranged to automate the insertion of a needle into the skin prior to the delivery of the medicament.

Injection devices generally comprise a drive mechanism which is arranged to automatically deliver a dose from the syringe, and optionally (in the case of an autoinjector) to first displace the syringe within the housing to cause needle penetration. The drive mechanism is typically released from an energised (or primed) position and may, for example, include one or more drive springs. The drive mechanism may act upon a plunger which includes or acts against a piston (also referred to as a "bung") which is slidably provided within the syringe. In the case of an autoinjector the initial stiction between the piston and syringe and the incompressibility of the medicament may resist forward movement of the piston relative to the syringe enabling the drive mechanism to initially move the syringe into the needle insertion position (whereupon further movement of the syringe is blocked and the drive mechanism will continue to move forward thus moving the piston). In other known devices additional features may be incorporated into the drive mechanism to force/control the sequencing of the needle insertion and drug delivery actions.

A trigger, for example in the form of a button on the end of the device, is generally provided to allow the user to activate the delivery sequence. It is known to provide a safety arrangement in the form of a mechanical lock (which, as is common in the art, shall be referred to herein as an "interlock") arranged to prevent actuation of the delivery mechanism by the user unless the lock is in the unlocked position. For example, such safety arrangements may require the user to perform a readying action prior to releasing the trigger or may be arranged to require the injection device to be in contact with an injection site before the trigger is able to activate the delivery mechanism. An example of a device including such an interlock arrangement is for example shown in the Applicants' earlier patent application PCT/GB2015/052852.

The provision of safety mechanisms is desirable to avoid inadvertent operation of injection devices (particularly, in auto-injectors where inadvertent operation could result in injury due to the projection of the needle during the insertion stage of the activation sequence). However, such arrangements may result in increased complexity of the device and potentially less intuitive use of the device for the end user. It will be appreciated that an interlock arrangement will normally be biased towards its unlocked position and the user must act against this bias when activating the device. Some users, such as the young or frail may experience difficulty, in activating a device which requires an interlock to be maintained in position whilst triggering the device.

Thus, it is desirable to provide an alternate injection device which may at least partially address some of these disadvantages.

SUMMARY OF THE INVENTION

Accordingly, in one aspect, this invention provides an injection device for delivering a dose of medicament from a syringe, the injection device comprising:
  a housing having a forward body and rearward body and wherein the forward and rearward body are axially moveably interconnected;
  a drive mechanism arranged, in use, to deliver a dose from said syringe;
  a trigger for activating the drive mechanism; and
  an interlock having a locked position, in which activation of the drive mechanism by the trigger is prevented, and an unlocked position, in which the drive mechanism may be activated, the interlock arrangement being moved to the unlocked position by relative axial movement of the forward and rearward body caused by the injection device being urged against an injection site; and characterised in that the injection device further comprises:
  an interlock hold arrangement associated with a forward facing skin abutment surface of the injection device and configured to help maintain the alignment of the rearward and forward body when the interlock is in the unlocked position and the forward facing skin abutment surface is in contact with an injection site.

The interlock may be biased (for example by an interlock spring) towards the locked position. The user may, typically, have to provide the relative axial movement of the forward and rearward body against the force of the bias when urging the device against an injection site. This force will generally need to be maintained until the trigger has been activated.

The drive assembly may be of the type which is released from an energised position (for example a compressed drive spring). The trigger may be associated with a latch which holds the drive assembly in the energised position prior to activation. The drive mechanism may be arranged to displace the syringe within the housing to cause needle penetration prior to the subsequent automatically delivery of a dose from the syringe The interlock hold arrangement provides an engagement between the rearward and forward housing to help maintain the alignment of the rearward and forward body when the interlock is in the unlocked position and the device is in contact with an injection site.

The engagement of the interlock hold arrangement is intended to assist maintenance of the interlock in the unlocked position. The engagement is only maintained whilst the device is in the unlocked interlock position and in contact with an injection site. The interlock hold arrangement may therefore be a reversible arrangement. The engagement of the interlock hold arrangement may be considered to be a temporary or holding engagement.

The interlock hold arrangement may be configured such that it is not able to maintain the alignment of the interlock without the additional force urging the device against an injection site. However, the interlock hold arrangement may provide assistance to the end user by reducing the force required to maintain the interlock in the unlocked position. The Applicant has recognised that this is particularly advantageous in improving operability without decreasing safety. In particular some users may be able to provide sufficient force to the device when presenting it to an injection site for use to initially move the interlock into the unlocked position but may then experience difficulty in maintaining the required force whilst also activating the trigger. For example users may simply forget that it is necessary to maintain the required alignment or may have difficulty due to limited strength or manual dexterity.

The interlock hold arrangement may comprise an engagement feature in one of the forward or rearward body. The hold arrangement may further comprise a cam surface, fixed relative to a forward facing skin abutment surface of the injection device. The cam surface may move into alignment with the engagement feature in the forward or rearward body when the interlock is in the unlocked position. The hold arrangement may further comprise a resilient member. The resilient member may be deflected by the cam surface so as to engage the engagement feature in the forward or rearward body.

It will be appreciated that the engagement feature may be selected dependent upon the design of the device. For example, in some embodiments the engagement feature may be a cutout or recess. Alternatively, the engagement feature may be a projection or boss.

The resilient member may be deflected radially, for example outwardly, into holding engagement with the engagement feature (for example into the cutout or recess). At least a forward portion of the rearward body may be radially outside of at least a rearward portion of the forward body. The forward portion of the rearward body may substantially surround the rearward portion of the forward body. The resilient member may be provided on the forward body (and the cutout or recess may be provided in the rearward body).

Alternatively the other of the forward or rearward body could include a further cutout which moves into alignment with the cutout or recess of the forward or rearward body. In such an arrangement the resilient member could act to hold the cutouts or recess in alignment (for example passing through one of the cutouts into engagement with the cutout or recess of the other body portion).

The resilient member may comprise a flexible tongue formed in the side wall of the other of the rearward or forward body.

The flexible tongue extends from a first end fixed relative to the body to a free end. The free end may be arranged to be resiliently deflected, in use, by the cam surface. The free end may be a forward end and the fixed end may be the rearward end. The flexible tongue may be integrally formed with the body (for example by a U-shaped cutout in the sidewall thereof).

The injection device may further comprise a shroud assembly at a forward end of the device. The forward facing skin abutment surface may be provided by a forward face of the shroud assembly. The shroud assembly may be forwardly biased and move rearwardly in response to the forward facing skin abutment surface being pressed against an injection site. The forward bias may move the shroud assembly to a forward position in response to relief of pressure urging the forward facing skin abutment surface against an injection site. It will be appreciated that "relief of pressure" would typically be caused by the full or partial removal of the device from the injection site (for example if the user chooses not to proceed with an injection). The forward movement may be a return to the initial pre-use position (for example if the device has not been activated) or may be a movement to a second forward position in which the needle is shrouded post injection.

The cam surface may be formed on the shroud assembly, for example on a rearward portion of the shroud assembly. Advantageously, this may provide a device in which the interlock hold arrangement is automatically released if the device is removed from contact with the injection site (since the cam surface will move out of alignment due to the movement of the shroud). Thus, in some embodiments the interlock hold arrangement may be configured to be released by forward movement of the shroud assembly caused by the relief of pressure urging the forward facing skin abutment surface against an injection site.

The interlock hold arrangement may comprise a plurality of interlock hold arrangements. For example the interlock hold arrangement may comprise a pair of radially opposed interlock hold arrangements.

The rearward body may be arranged to be held by the user during use. The rearward body may be configured to slide forwardly relative to the forward body when the injection device is pressed against an injection site. The trigger may comprise a button associated with the rear body.

Whilst the invention has been described above, it extends to any inventive combination of the features set out above, or in the following description or drawings.

BRIEF DESCRIPTION OF THE DRAWINGS

The invention may be performed in various ways, and an embodiment thereof will now be described by way of example only, reference being made to the accompanying drawings, in which.

DETAILED DESCRIPTION OF EMBODIMENTS

Front as used herein will be understood to refer to the end of the injector assembly (or components thereof) which, in use, are closest to the delivery needle delivery end of the injector (i.e. the end which is pointed at the skin). Rear as used herein will be understood to refer to the end of the pen injector assembly (or components thereof) which, in use, are furthest from the needle delivery end of the injector (i.e. the end which is pointed away from the skin). Forward and rearward will, likewise, be understood to refer to the directions orientated towards the front and rear of the injector assembly.

Axial, radial and circumferential may be used herein to conveniently refer to the general directions relative to the longitudinal direction of the injection device (or components thereof). The skilled person will, however, appreciated that these terms are not intended to be narrowly interpreted (and for example, the injection device may have a non-circular and/or irregular form). Typically, regardless of the chosen injector device external profile the cartridge or syringe will have a conventional generally cylindrical form and, as such, the longitudinal axis of the injection device will normally substantially coincide with (or be parallel to) the axial direction of the syringe.

Figure 1:
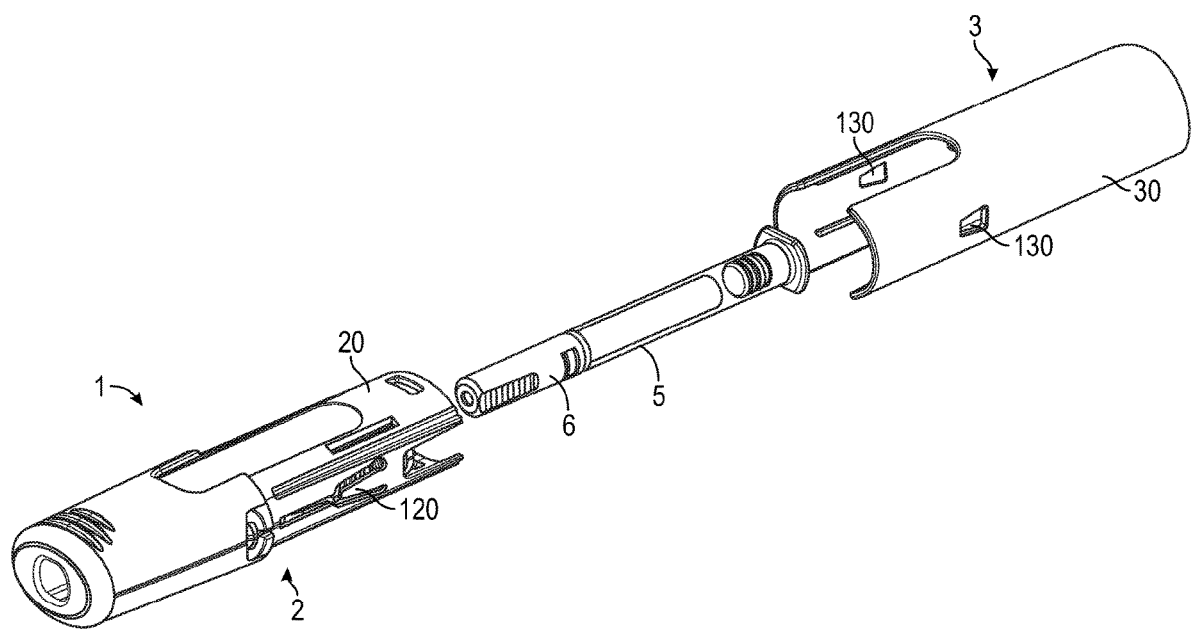
FIG. 1 is an exploded view of an autoinjector incorporating features in accordance with the present invention.

As seen in FIG. 1, an autoinjector 1 in accordance with an embodiment of the invention comprises a housing defined by a forward body 20 and a rearward body 30. A syringe 5 of medicament is provided within the housing. The housing 20, 30 has a generally elongate tubular shape with a substantially oval cross-sectional profile.

The syringe is a conventional syringe having a bung or stopper 7 within its body and a needle at its forward end which may initially be protected (so as to remain sterile) by a removable needle shield 6. The illustrated autoinjector 1 is generally intended to be a single use device (although the skilled person will appreciate that the invention is not limited to such devices) and, therefore, the exploded view of FIG. 1 may typically represent a final assembly stage in which the syringe is placed into the housing (for example in a manufacturing facility). The end user would typically be provided with the autoinjector 1 preassembled around the syringe 5. The autoinjector may conveniently be arranged during manufacture into a forward sub-assembly 2, comprising the forward body 20 and those components which are initially forward of the syringe 5, and a rearward sub-assembly 3, comprising those components which are initially rearward of the syringe 5.

Figure 2:
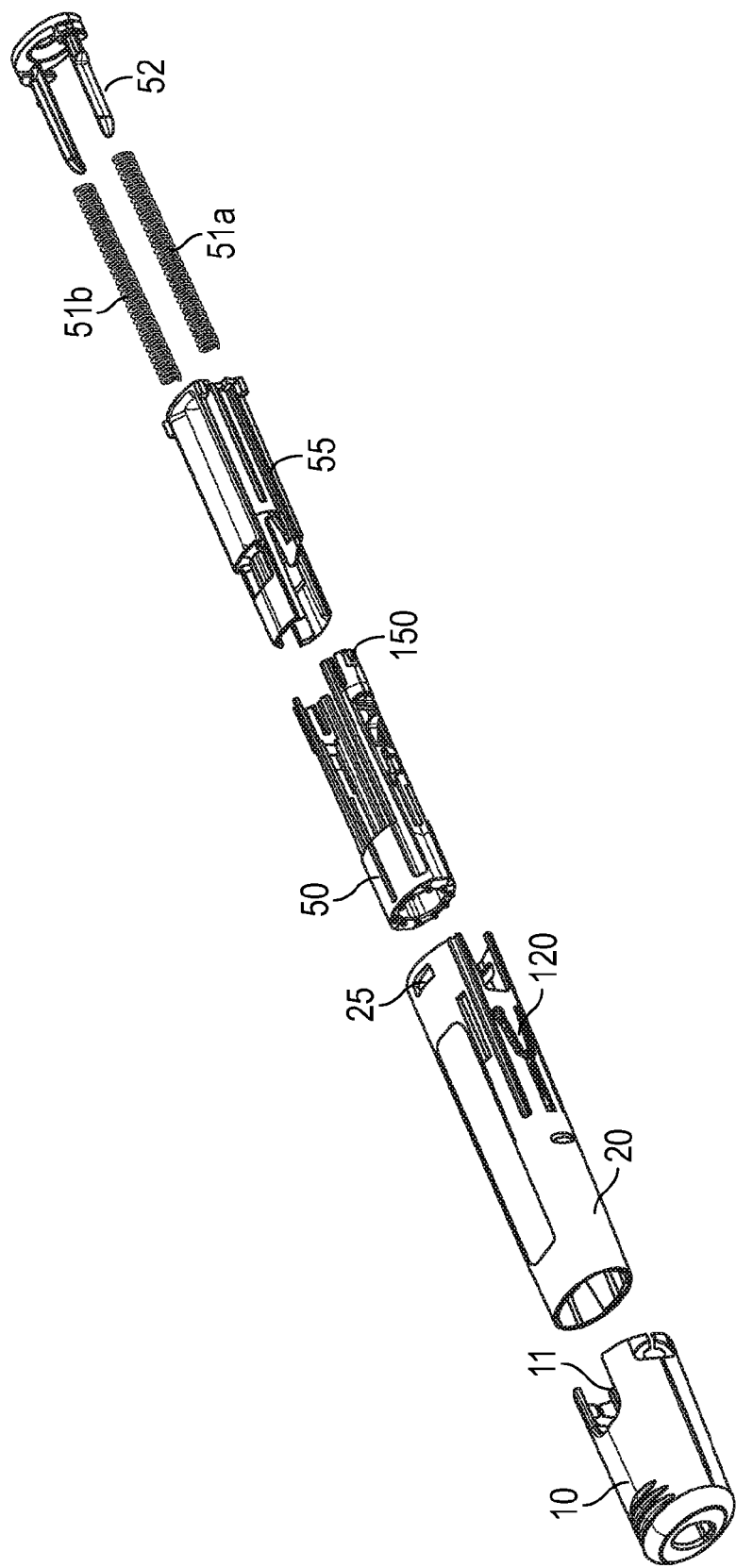
FIG. 2 is an exploded view of the forward sub-assembly of the autoinjector device of FIG. 1.
Figure 3:
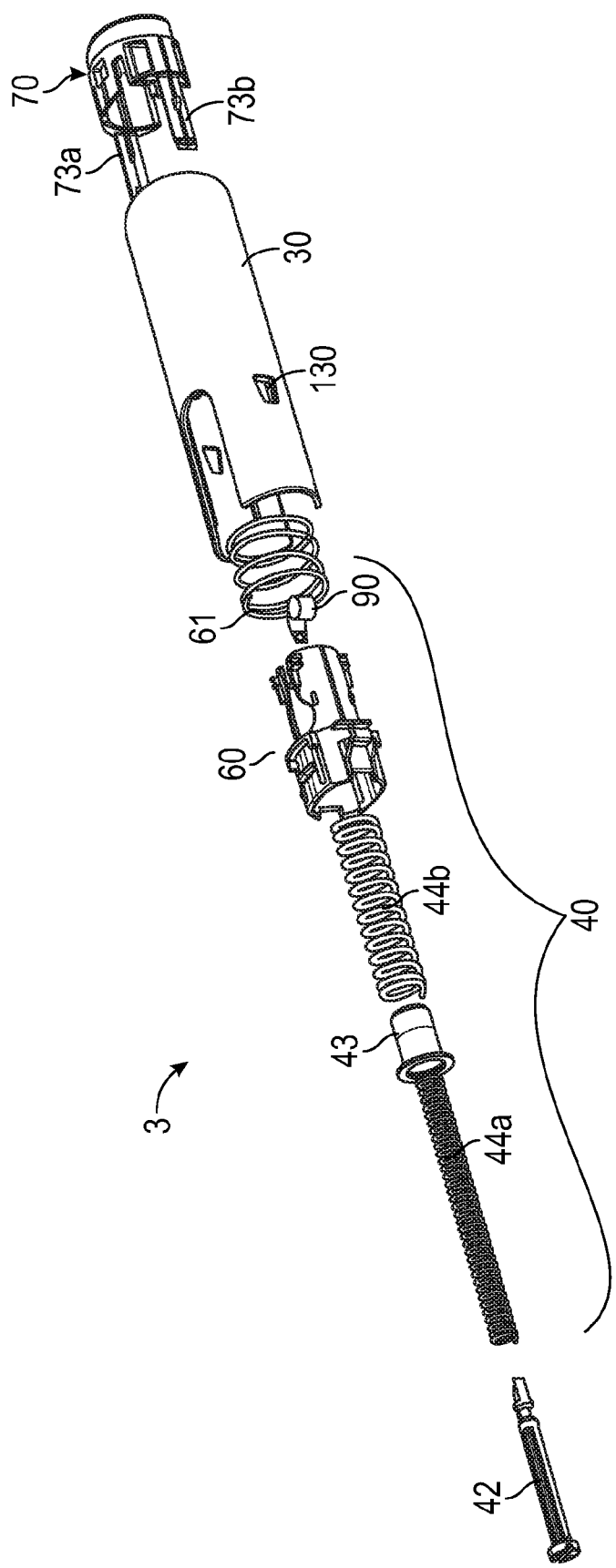
FIG. 3 is an exploded view of the rearward subassembly of the autoinjector device of FIG. 1.

An exploded view of each of the forward and rearward sub-assemblies are shown in FIGS. 2 and 3.

The forward sub-assembly 2 comprises the forward body 20 which is adapted to receive a cap 10 which closes the forward end of the autoinjector 1. The cap 10 may include an internal formation, comprising rearwardly extending members 11, arranged to engage the removable needle shield 6 of the syringe 5 such that removal of the cap 10 from the forward housing 20 during use also removes the removable needle shield 6 from the syringe 5. Within the sub-assembly 2 there is a syringe carrier 55 for movably mounting the syringe within the forward body 20 to enable automatic needle penetration. It may be noted that prior to the removal of the cap 10, the rearwardly extending members 11 of the cap 10 underlie spring fingers 56 of the syringe carrier 55. This arrangement, thus prevents inward movement of the spring fingers 56 prior to removal of the cap 10 and, therefore, blocks unlatching of the syringe carrier 55 and prevents movement relative to the forward body 20.

A needle shroud 50 is also provided and arranged to shroud the needle after use (when the syringe 5 and syringe carrier 55 are in a forward position) to prevent needle stick injuries. The shroud 50 is activated by a pair of side-by-side shroud springs 51a, 51b carried on a spring guide 52. Whilst, the present application is not limited to any specific arrangement of the syringe carrier 55 and/or needle shroud 50, it may be noted that the arrangement substantially corresponds to the arrangement of the Applicants' earlier International Patent Application PCT/GB2011/052557.

The rearward sub assembly 3 includes a trigger button 70 which is inserted into the rearward housing 30 from the rearward end so as to substantially close the rearward end of the injector housing. The trigger button 70 has a cup-like profile with side walls which are arranged to fit within (and be substantially concentric with) the rearward housing 30 and an end wall which closes the rear end of the housing. The trigger button includes a pair of forwardly extending resilient arms 73a and 73b which are arranged to provide an engagement between the trigger button 70 and the injector 1, as will be described in greater detail below. For ease of manufacture and assembly the trigger could be comprised of a sub assembly of parts; however in the embodiment shown in FIG. 3 the trigger button comprises a single moulded part.

The rearward sub-assembly 3 also includes the drive mechanism 40. The drive mechanism 40 includes a plunger 42 which is arranged to engage the bung of the syringe in use. The invention is not limited to any specific drive mechanism but the basic functional operation of the drive mechanism 40 is substantially as described, for example, in the Applicants' earlier International Patent Applications PCT/GB2011/051950 and PCT/GB2014/052276. The plunger 42 is driven forwards in use by a pair of concentric drive springs 44a and 44b (although it will be appreciated that in other embodiments a single spring may be used) with an intermediate drive member 43 provided therebetween. A latch 60 is arranged concentrically around the drive springs 44, intermediate member 43 and plunger 42. The latch 60 is arranged to hold the plunger 42 against the bias of the springs 44 until the latch is released via the trigger button 70 (when both drive springs and the intermediate drive member are all released together). The latch 60 comprises a rear body portion 60b having a split cylinder profile and defining a latch aperture at its rear end and a forward connecting body portion 60b. The forward body portion 60a has an external profile substantially corresponding to the interior profile of the rearward end of the forward housing 20.

For safety an interlock arrangement is provided which blocks the release of the latch 60 by the trigger button 70 unless the interlock is in an unlocked state. The interlock arrangement is moveable between a locked and an unlocked state by relative forward sliding movement of the rear body portion 30 relative to the front body portion 20. Specifically, in use the user will grasp the device 1 by the rear body portion 30 and press the forward end of the device (i.e. of the forward assembly 2) against an injection site. An interlock spring 61 is provided which biases the body portions 20, 30 apart and therefore normally maintains the interlock in the locked position. The unlocking of the interlock acts against the force of the interlock spring 61. The interaction between the interlock and the drive mechanism may for example be as described in the Applicants' earlier patent application PCT/GB2015/052852. The skilled person will appreciate that interlock arrangements as such are known and that other other interlock arrangements which utilise a relative movement between housing portions are possible. Accordingly, the application of embodiments of the invention is not intended to be limited to any specific interlock arrangement.

In accordance with an embodiment of the invention the injection device 1 is provided with an interlock hold arrangement 100 which assists the end user in maintaining the device 1 in the correct alignment for actuation until they have activated the trigger 70. The interlock hold arrangement 100 comprises a cutout window 130 in the side wall of the rearward body housing 30, a flexible tongue 120 formed in the sidewall of the forward body housing 20 and an outwardly directed radial projection or tab 150 at a rearward end of the shroud 50. In the illustrated embodiment a pair of interlock hold arrangement 100*a* and 100*b* are provided at radially opposed locations on the device 1 (for simplicity the operation of a single interlock hold arrangement will be described below but it will be appreciated that each hold arrangement 100*a*, 100*b* operates in parallel and in an identical manner).

The cutout 130 is a simple through window in the sidewall of the rearward body housing 30. Alternatively a corresponding feature could be provided in the form of a blind recess in the inner surface of the side wall.

The flexible tongue 120 may be formed by a U-shaped cut out in the side wall of the forward body housing 20. Thus, the tongue 120 may extend in a generally axial direction from a rearward end which is contiguous with the side wall of the forward body housing 20 to a free end which is separate from the side wall. As the forward body housing 20 is formed from a plastic material the tongue 120 may resiliently deflect from its natural position (in which it is substantially co-planar with the surrounding side wall).

The tab 150 may be formed on any conveniently located section of the shroud 50 (with the other features of the interlock hold arrangement 100 aligned accordingly). The tab 150 extends radially outwardly and is provided with outwardly tapered forward 152 and rearward 151 facing surfaces.

Figure 4:
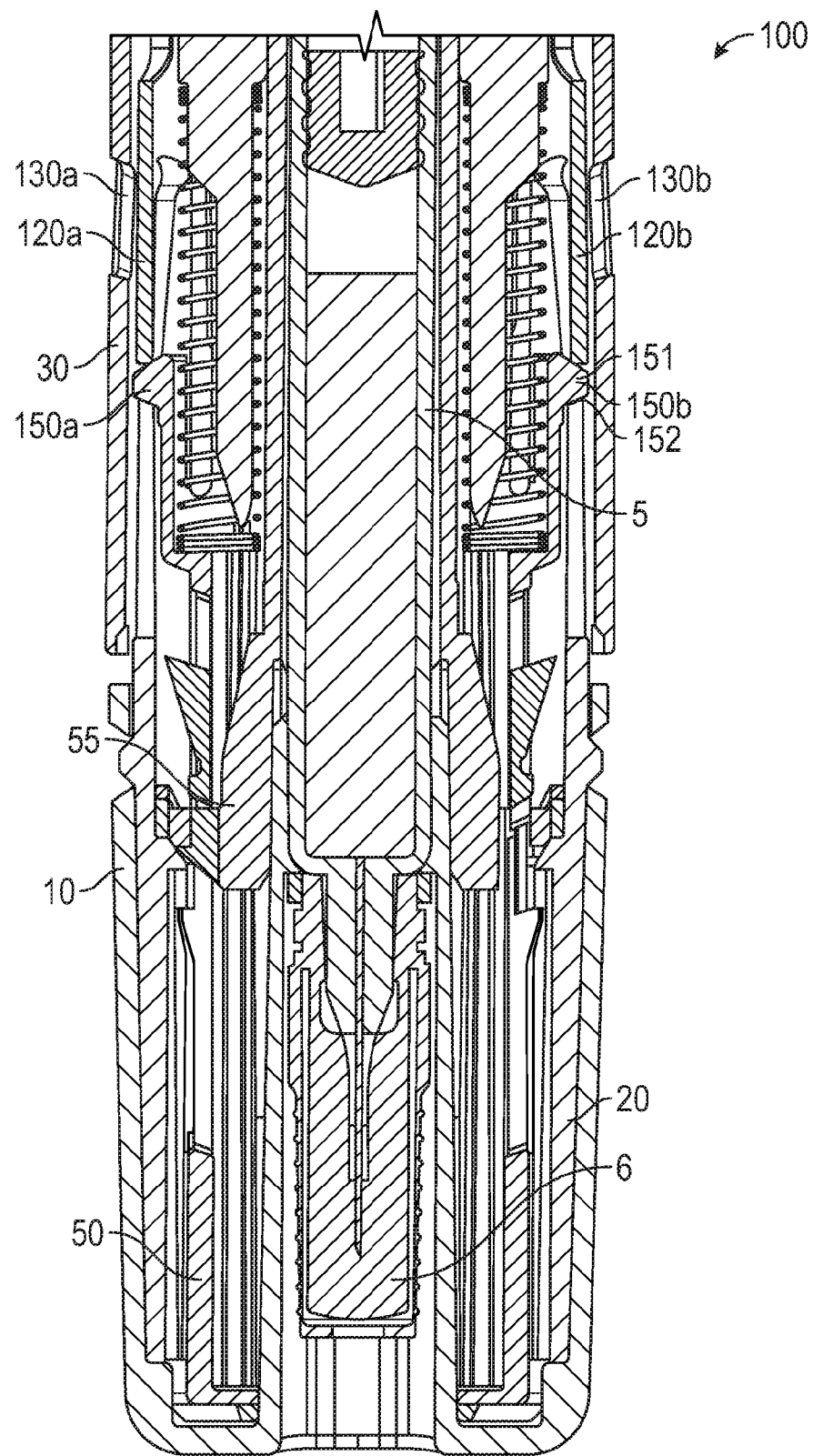
FIG. 4 shows a cross-sectional view of the forward end of an injection device in accordance with a first embodiment of the invention in a pre-use configuration.

As shown in FIG. 4, in an initial configuration with the cap 10 positioned on the device 1, the interlock hold arrangement 100 is inactive. The tab 150 is positioned forward of the front end of the flexible tongue 120 (and is seated in a cutout formed ahead of the forward end thereof and the side wall of the forward body housing 20). The cutout 130 of the rearward housing is rearward of the flexible tongue 120 and tab 150.

Figure 5:
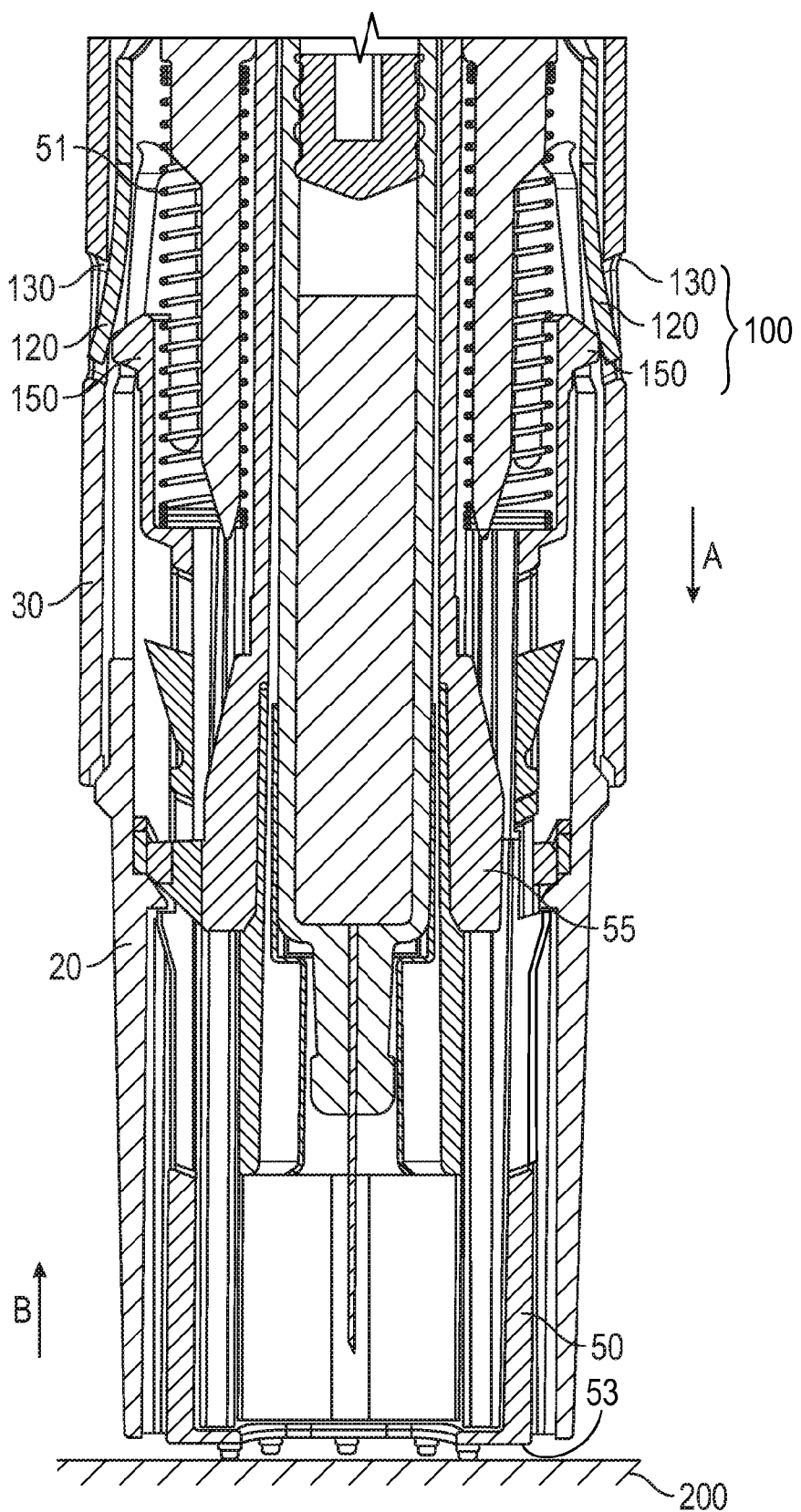
FIG. 5 shows a cross-sectional view of the device of FIG. 4 in a pre-activation configuration.

The user readies the device 1 by removing the cap 10 before pressing the forward end of the device against an injection site 200 as shown in FIG. 5. The user will grip the rearward housing 30 during use. As the skin abutment surface 53 at the forward end shroud 50 is initially positioned slightly forward of the forward housing 20 (see FIG. 4) and biased forwardly by the shroud springs 151, upon initial contact with the skin it is moved rearwardly as shown by arrow B. As the user urges the device against the injection site 200, the rearward housing 30 is also moved forward relative to the forward housing 20 as shown by arrow A. The relative movement between the housing portions 20, 30 brings the window 130 of the rearward body housing 30 into alignment with the flexible fingers 120 of the forward housing 20. Due to the rearward movement of the shroud assembly 50 the tab 150 moves rearwardly relative to the flexible tongue 120 of the forward housing 20. This movement causes the flexible fingers to ride over the sloped rearward surface 151 of the tab 150 and be cammed outwardly. As a result the flexible finger 120 deflects radially outwardly into the window 130. Thus, in this configuration the interlock hold arrangement 100 is active. The positioning of the components 120, 130, 150 of the interlock hold arrangement 100 are selected such that this position corresponds to the position in which the relative movement between for forward 20 and rearward housing portions has also been sufficient to move the interlock to its unlocked position.

With the interlock hold arrangement 100 in the active position of FIG. 5 it will be seen that should the force provided by the user on the rearward housing decrease the forward end of the flexible tongue 150 will resist any rearward movement of the rearward body housing 30. It may also be noted that the outward incline of the tongue 120 may provide a barb type effect in this direction. This assists the user in keeping the appropriate alignment between the body housing portions until the device has been triggered. However, in the event that the user chooses not to proceed with an injection and removes the device from the injection site 200 without triggering the drive mechanism it will be noted that the shroud 50 will return to its forward position moving the tabs 150 forward and enabling the flexible tongues 120 to return to their inward position. Thus, the interlock hold arrangement 100 does not affect the safety of the device as once removed from the injection site 200 the interlock will operate normally.

Figure 6:
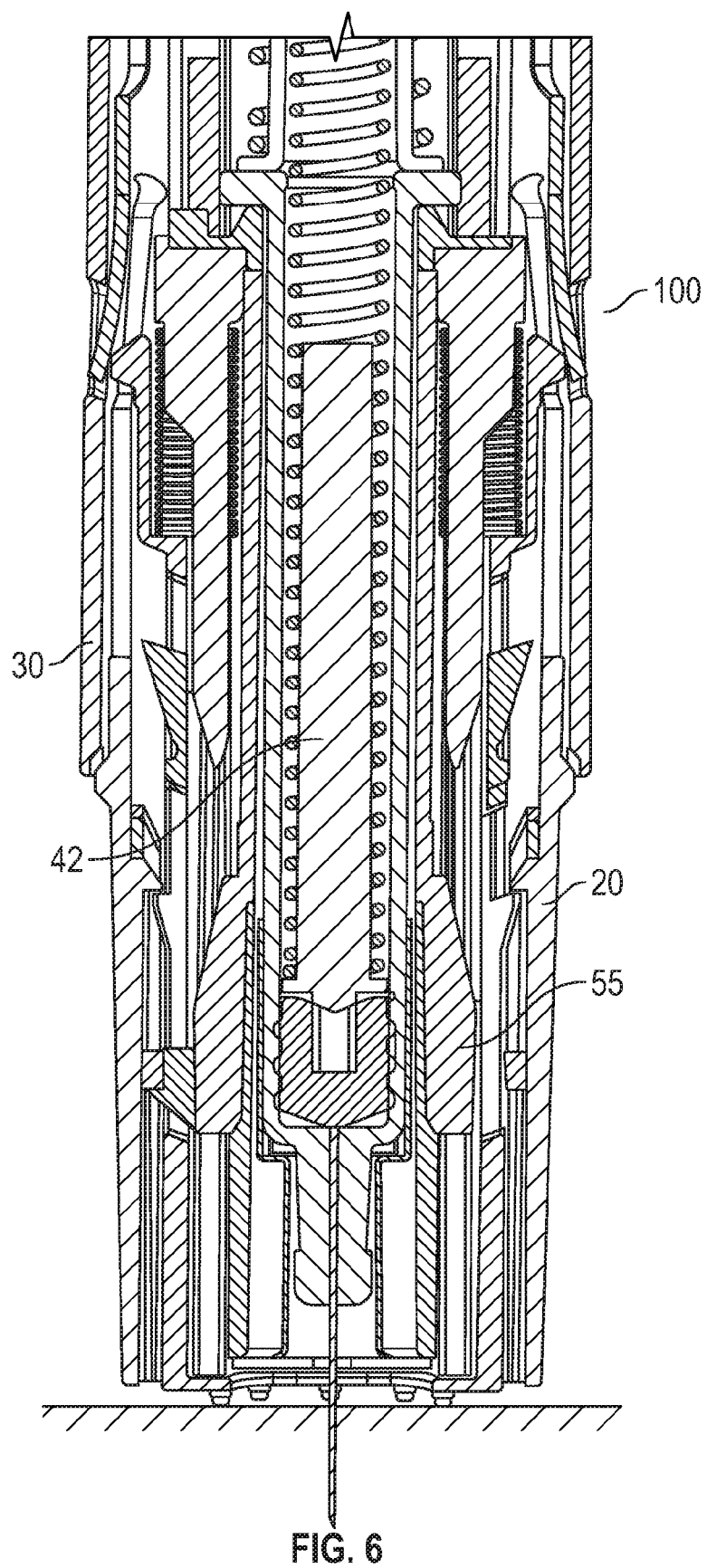
FIG. 6 shows a cross-sectional view of the device of FIG. 4 in a post-activation configuration.
Figure 7:
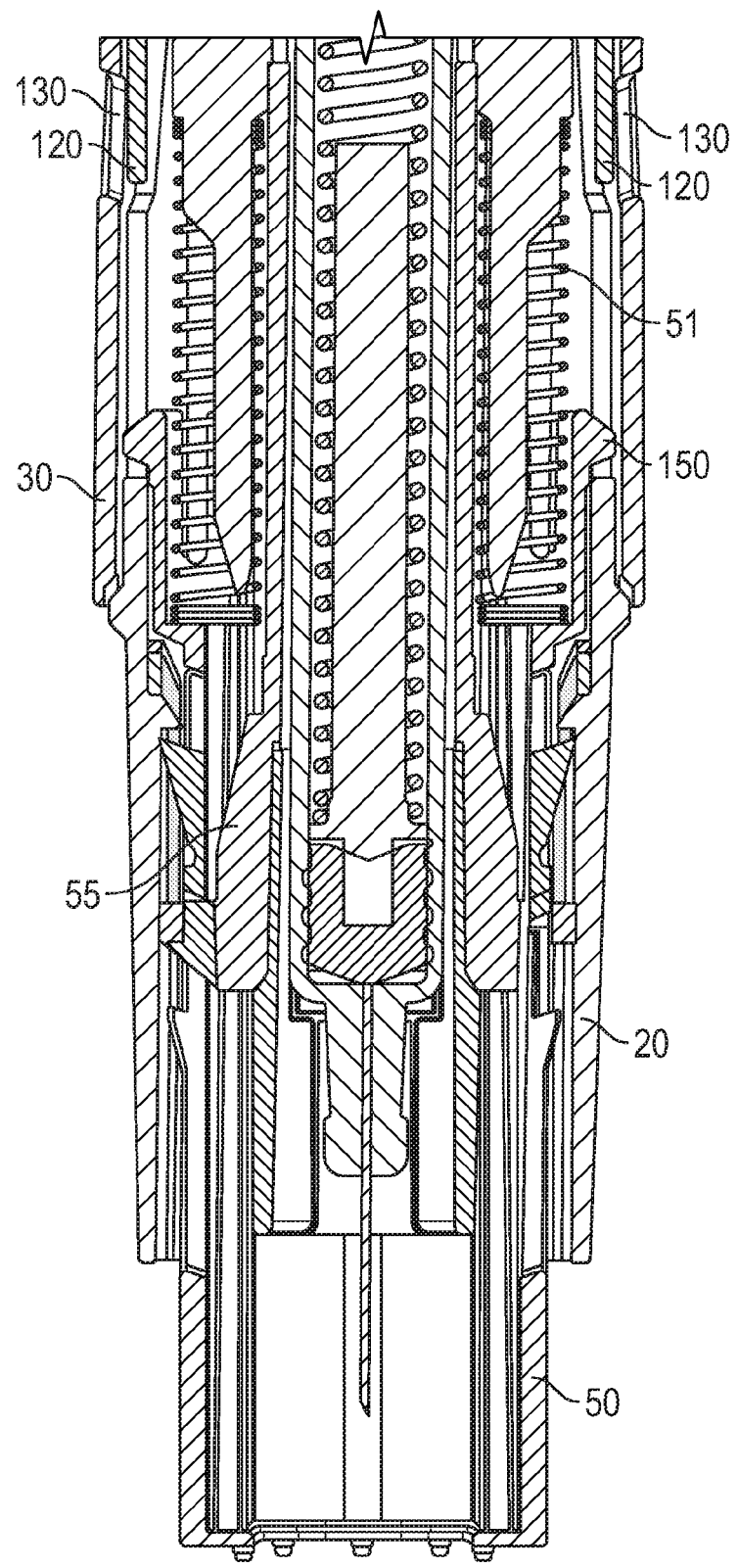
FIG. 7 shows a cross-sectional view of the device of FIG. 4 in a safe configuration following removal from the injection site.

FIG. 6 shows the configuration of the device immediately after delivery of a dose (but prior to removal from the injection site 200). In this state the interlock hold arrangement 100 is still in its active configuration (but the user has already triggered). As explained in the applicants' earlier International Patent Application PCT/GB2011/052557 during triggering of the injection the syringe is carried forward in the syringe carrier 55 and acts to release the shroud 50 for subsequent forward movement. The user then removes the device 1 from the injection site 200 withdrawing the needle as shown in FIG. 7. The shroud is forced forward by the shroud springs 51 and locks out in the position shown so as to make the needle safe. The forward movement of the shroud also acts to displace the tab 150 forward of the flexible tongues 120 such that the interlock hold arrangement 100 is no longer active.

Figure 8:
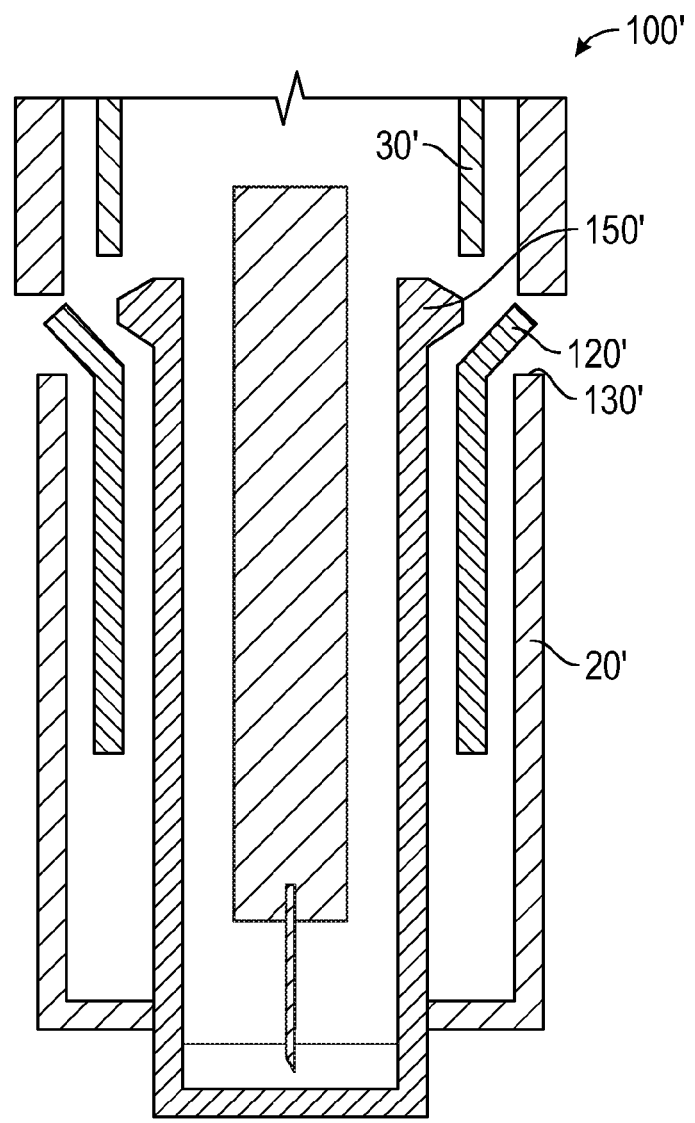
FIG. 8 schematically shows an alternative embodiment of the invention.

For completeness, an alternative embodiment is shown schematically in FIG. 8 to demonstrate that the arrangement of the cutout and resilient member of the invention could be reversed without altering the underlying function of the interlock hold arrangement 100' (and depending upon the particular arrangement of the injection device to which an embodiment of the invention is being applied). In this embodiment, the forward body housing 20' is positioned on the exterior of the rearward housing 30'. Accordingly, the rearward housing 30' is provided with a resilient tongue 120' and the forward housing 20' is provided with a cutout window 130'. The interlock hold arrangement 100' operates in the same manner with a tab 150' displacing the tongue 120' when aligned so as to engage the cutout 130'. In contrast to the previous embodiment it may be noted that the free end of the tongue 120' is the rearward end but this arrangement could be reversed.

The interlock hold arrangement 100 in accordance with an embodiment of the invention may typically be a passive arrangement in the sense that it is activated without any action being required by the user. The user may generally be unaware of the features during use but will benefit from the assistance in maintaining the correct relative position of the forward and rearward housing portions. However, if required it will also be appreciated that the interlock hold arrangement could provide an indication of the interlock being moved to the unlock position—for example the flexible tongue may be readily visible through the cutout window or the interlock hold arrangement may provide an audible or tactile indication (such as a click) when in the active position.

Although the invention has been described above with reference to a preferred embodiments, it will be appreciated that various changes or modifications may be made without departing from the scope of the invention as defined in the appended claims.

The invention claimed is:

1. An injection device for delivering a dose of medicament from a syringe, the injection device comprising:
    a housing comprising a forward body and a rearward body, the forward body and the rearward body being axially moveably interconnected;
    a drive mechanism comprising a plunger arranged to deliver a dose from the syringe when the injection device is in use;
    a trigger for activating the drive mechanism;
    an interlock having a locked position in which activation of the drive mechanism, by the trigger, is prevented and an unlocked position in which the drive mechanism may be activated, the interlock being moved to the unlocked position by relative axial movement of the forward body and the rearward body caused by the injection device being urged against an injection site; and
    an interlock hold arrangement comprising a first interlocking component on the forward body and a second interlocking component on the rearward body,
        the relative axial movement of the forward body and the rearward body moving the first interlocking component on the forward body into alignment with the second interlocking component on the rearward body prior to delivery of the dose from the syringe such that the first interlocking component moves from a non-engaged position to an engaged position with the second interlocking component,
        the interlock hold arrangement being associated with a forward facing skin abutment surface of the injection device and configured to prevent rearward movement of the rearward body relative to the forward body when the first interlocking component and the second interlocking component are engaged with one another, the interlock is in the unlocked position, and the forward facing skin abutment surface is in contact with the injection site, and
        wherein movement of the first interlocking component from the non-engaged position to the engaged position with the second interlocking component occurs prior to forward movement of the trigger.

2. The injection device of claim 1, wherein the first interlocking component of the interlock hold arrangement comprises a first engagement feature comprising a resilient member in the forward body and the second interlocking component of the interlock hold arrangement comprises a second engagement feature in the rearward body; and
    wherein the interlock hold arrangement further comprises a cam surface, fixed relative to the forward facing skin abutment surface of the injection device, which moves into alignment with the first engagement feature when the interlock is in the unlocked position; and
    wherein the resilient member is deflected by the cam surface so as to provide a holding engagement with the second engagement feature.

3. The injection device of claim 2, wherein the resilient member is deflected radially outwardly into the holding engagement with the second engagement feature.

4. The injection device of claim 2, wherein the resilient member comprises a flexible tongue formed in a side wall of the forward body.

5. The injection device of claim 2, wherein the second engagement feature comprises a cutout or recess.

6. The injection device of claim 4, wherein the flexible tongue extends from a rearward end and is fixed relative to the forward body, to a free forward end which may be resiliently deflected by the cam surface, when the injection device is in use.

7. The injection device of claim 2, wherein the injection device further comprises a shroud assembly at a forward end of the injection device.

8. The injection device of claim 7, wherein the shroud assembly is subjected to a forward bias and moves rearwardly in response to the forward facing skin abutment surface being pressed against an injection site.

9. The injection device of claim 8, wherein the forward bias moves the shroud assembly to a forward position in response to relief of pressure urging the forward facing skin abutment surface against an injection site.

10. The injection device of claim 7, wherein the cam surface comprises a tab formed on the shroud assembly.

11. The injection device of claim 10, wherein the interlock hold arrangement is released by forward movement of the shroud assembly caused by the relief of pressure urging the forward facing skin abutment surface against an injection site.

12. The injection device of claim 1, wherein the interlock hold arrangement is a first interlock hold arrangement, and
    wherein the injection device further comprises a second interlock hold arrangement which is radially opposed to the first interlock hold arrangement,
        the second interlock hold arrangement comprising a third interlocking component on the forward body and a fourth interlocking component on the rearward body.

13. The injection device of claim 1, wherein the rearward body is arranged to be held by a user during use and to move forwardly relative to the forward body when the injection device is pressed against the injection site.

14. The injection device of claim 1, wherein the trigger comprises a button associated with the rearward body.

15. The injection device of claim 7, wherein the forward facing skin abutment surface is provided by a forward face of the shroud assembly.

* * * * *